United States Patent
Bunel

(12) 
(10) Patent No.: US 6,175,043 B1
(45) Date of Patent: *Jan. 16, 2001

(54) PROCESS OF PREPARATION OF LINEAR ALDEHYDES

(75) Inventor: Emilio Enrique Bunel, Wilmington, DE (US)

(73) Assignees: E. I. du Pont de Nemours and Company, Wilmington, DE (US); DSM N.V., Galeen (NL)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/210,232

(22) Filed: Dec. 11, 1998

Related U.S. Application Data

(63) Continuation-in-part of application No. 08/902,508, filed on Jul. 29, 1997, now abandoned.

(51) Int. Cl.[7] .................................................. C07C 45/50
(52) U.S. Cl. ........................................ 568/454; 568/451
(58) Field of Search ................................... 568/451, 454; 502/121, 162, 213

(56) References Cited

U.S. PATENT DOCUMENTS

| | | | |
|---|---|---|---|
| 4,148,830 | 4/1979 | Pruett et al. | 260/604 HF |
| 4,247,486 | 1/1981 | Brewester et al. | 568/454 |
| 4,668,651 | 5/1987 | Billig et al. | 502/158 |
| 4,717,775 | 1/1988 | Billig et al. | 568/454 |
| 4,769,498 | 9/1988 | Billig et al. | 568/454 |
| 4,885,401 | 12/1989 | Billig et al. | 568/454 |
| 5,059,710 | 10/1991 | Abatjoglou et al. | 558/78 |
| 5,113,022 | 5/1992 | Abatjoglou et al. | 568/454 |
| 5,235,113 | 8/1993 | Sato et al. | 568/454 |
| 5,264,616 | 11/1993 | Roeper et al. | 560/175 |
| 5,512,695 | 4/1996 | Kreutzer et al. | 558/338 |
| 5,648,554 | 7/1997 | Mori et al. | 568/454 |
| 5,710,344 | * 1/1998 | Breikss | 568/454 |

FOREIGN PATENT DOCUMENTS

| | | | |
|---|---|---|---|
| 0 633 062 A1 | 4/1994 | (EP) | B01J/31/16 |
| WO 93/03839 | 3/1993 | (WO) | B01J/31/24 |
| WO 95/18089 | 7/1995 | (WO) | C07C/69/716 |

* cited by examiner

Primary Examiner—Sreeni Padmanabhan

(57) ABSTRACT

The present invention provides an improved hydroformylation process in which the catalyst system is composed of a Group VIII metal and organic phosphite ligand having the structure $P(OR)_2$-OR'O—$P(OR)_2$ or $P(OR)_3$, where R and R' are organic residues which may be the same or different and where the R or R' contain at least one C9 to C40 aliphatic group positioned as a tail extending away from the primary ligand structure rendering the ligand lipophilic.

15 Claims, No Drawings

PROCESS OF PREPARATION OF LINEAR ALDEHYDES

This application is a continuation-in-part of the earlier filed and co-pending application numbered Ser. No. 08/902,508 filed on Jul. 29, 1997, now abandoned.

FIELD OF THE INVENTION

This invention relates to a process for the preparation of linear aldehydes by hydroformylation of ethylenically unsaturated organic compounds in the presence of a catalyst system comprising a Group VIII metal and an organic ligand containing phosphorous having the structure $P(OR)_2$-$OR'O$—$P(OR)_2$ or $P(OR)_3$, where R and R' are organic residues which may be the same or different and where the R or R' contain at least one C9 to C40 aliphatic group positioned as a tail extending away from the primary ligand structure rendering the ligand lipophilic.

BACKGROUND OF THE INVENTION

The synthesis of an aldehyde by hydroformylation is known in the art. A catalyst for such a process is generally a soluble complex of a Group VIII transition metal having a phosphorus containing organic ligand. It is also known that the selection of the catalyst for the hydroformylation reaction has an influence on the rate and selectivity to the product aldehyde(s). Bidentate ligands are particularly preferred for their combination of reactivity and selectivity.

A number of patents teach structures of bidentate ligands for hydroformylation reactions that may be used for the production of aldehydes. U.S. Pat. No. 5,235,113 teaches a hydroformylation process in which an organic bidentate phosphite ligand containing two phosphorus atoms linked with an organic dihydroxyl bridging group is used with rhodium as a homogeneous hydroformylation catalyst.

Hydroformylation processes involving organic bidentate ligands containing two trivalent phosphorus atoms, in which the two phosphorus atoms are linked with a 2,2'-dihydroxyl-1,1'-binaphthalene bridging group, have been described in U.S. Pat. Nos. 4,769,498, 4,668,651, 5,113,022, 5,059,710, 5,264,616, and 4,885,401. Additional examples appear in WO-A-9303839 and WO-A-9518089.

With respect to the hydroformylation process, U.S. Pat. No. 4,148,830 teaches the use of high boiling condensation products of the process as the solvent in recycling the catalyst system; and U.S. Pat. No. 4,247,486 teaches the use of a gas recycle to control the liquid level in the reaction and to control the build-up of high boiling components in the process stream.

These prior patents teach catalyst structures and improvements in continuous processes for hydroformylation, but none address the problem of isolating product, byproduct and catalyst, one from the other. Yet, in all hydroformylation processes, the catalyst must be separated from the reaction products. In the case of hydroformylations such as the present invention, where the desired reaction product is an aldehyde, it has proved difficult to separate reaction products, particularly the higher boiling products and byproducts, from the catalyst system.

U.S. Pat. No. 5,648,554 to Mori et al., teaches separation of the hydroformylation catalyst precursor and the high boiling byproducts by extraction of this mixture in a polar solvent. This patent does not demonstrate the proposed process with the actual catalyst system used in hydroformylation, and neither does this patent make any clear teaching as to ligand structures that are necessary for the process of the patent to be workable.

The present invention provides a process by which the reaction products, including the high boiling products and byproducts, may be easily separated from the reaction catalyst system. In the present process the catalyst system may be readily separated from reaction products and recycled for use in the process, thus providing longer active catalyst system productivity.

SUMMARY OF THE INVENTION

The present invention provides a process for preparation of a linear aldehyde comprising reacting an ethylenically unsaturated compound by hydroformylation in the presence of a catalyst system composed of a Group VIII metal and an organic phosphite ligand in a two phase reaction solvent. The organic ligand is one containing phosphorous having the structure $(PR_2)_n R'$ where n is an integer from 1 to 2, R and R' are organic residues which may be the same or different and where the R or R' contain at least one C9 to C40 aliphatic group positioned as a tail extending away from the primary ligand structure rendering the ligand lipophilic.

The preferred ligand is a bidentate phosphite ligand, $P(OR)_2$-$OR'O$—$P(OR)_2$ or $P(OR)_3$, where, containing at least one C9 to C40 aliphatic group positioned on the backbone or side arm ring structures of the ligand. The hydroformylation reaction solvent is preferred to be a two phase mixture of an organic compound having from 5 to 20 carbon atoms and polar solvent, but the present invention also applies to single phase reaction mixtures.

The present process may be represented as a series of process steps comprising:

(a) reacting in a reaction solvent to form a reaction mixture the ethylenically unsaturated compound in the presence of a catalyst system composed of a Group VIII metal and organic phosphite ligand containing phosphorous having the structure $P(OR)_2$-$OR'O$-$P(OR)_2$ R and R' are organic residues which may be the same or different and where the R or R' contain at least one C9 to C40 aliphatic group positioned as a tail extending away from the primary ligand structure rendering the ligand lipophilic;

(b) adding a non-polar solvent to the reaction mixture to form two phases, one a polar phase predominately formed from the reaction products and one formed predominately from the non-polar solvent and the catalyst system such that the reaction products including the high boiling reaction products of the hydroformylation remain in the polar phase and the catalyst system is partitioned substantially into the non-polar phase; and (c) separating the two phases and isolating the reaction products from the polar phase and the catalyst from the non-polar phase.

The preferred ligand a bidentate phosphite ligand having the structure $P(OR)_2$-$OR'O$—$P(OR)_2$ where R and R' are organic residues and where the R or R' contain at least one C9 to C40 aliphatic group positioned as a tail extending away from the bridging group (R') or the side arms (R).

Volatiles may be removed in the present process from the reaction mixture of step (a) before the addition of the non-polar solvent of step (b). Also in the present process steps (a) and (b) may be combined and such that the hydroformylation is carried out in a two phase reaction solvent.

The present process may be run as a batch or a continuous process. In a continuous process the recovered catalyst is returned to step (a) and the steps are repeated.

The present process also provides an improved hydroformylation process for preparation of a linear aldehyde from a reaction mixture containing an ethylenically unsaturated compound and a catalyst system composed of a Group VIII metal and a bidentate organic phosphite ligand having two trivalent phosphorous atoms wherein the ethylenically unsaturated compound also functions as reaction solvent, the improvement comprising: forming the catalyst system from a ligand containing at least one C9 to C40 aliphatic group positioned on the backbone or side arm ring structures of the ligand and following hydroformylation of the ethylenically unsaturated compound adding to the reaction mixture a two phase solvent mixture consisting of a polar and a non-polar components so that the reaction products of the hydroformylation are extracted into the polar phase of the solvent mixture and the catalyst system remains substantially in the non-polar phase of the solvent mixture.

Preferred structures for the phosphite ligands of the present invention are Ligands I–IX. As noted below the basic structure for Ligands I, II and III is the structure on the left (structure A); the basic structure for Ligands IV to IX is the structure on the right (structure B)

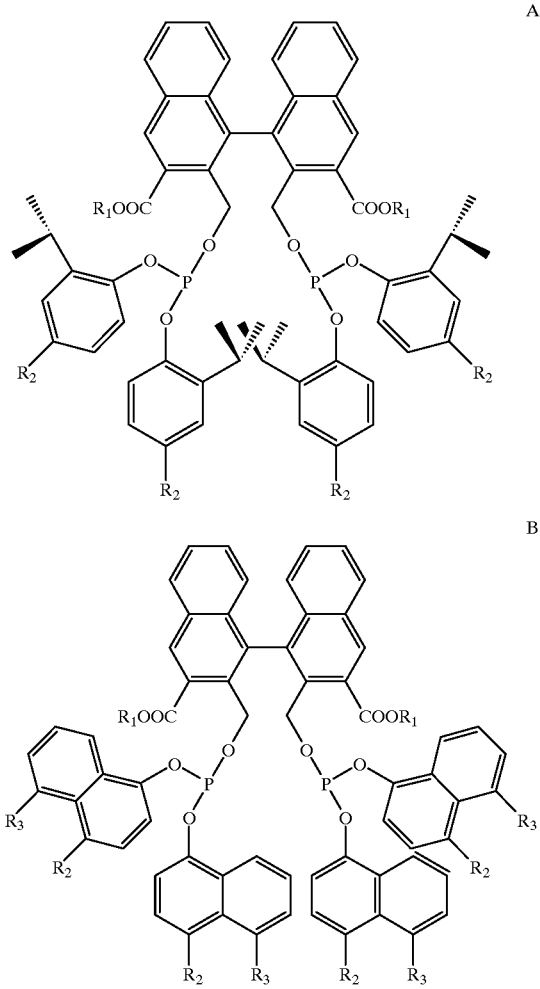

wherein structures A for Ligands I to III and structures B for Ligands IV to IX, Ligand I, $R_1$ is $(CH_2)_9CH_3$ and $R_2$ is H; Ligand II, $R_1$ is $(CH_2)_9CH_3$ and $R_2$ is $CO(CH_2)_8CH_3$; Ligand III is $R_1$ and $R_2$ are $(CH_2)_9CH_3$; Ligand IV, $R_1$ is $(CH_2)_9CH_3$, $R_2$ is $O(CH_2)_9CH_3$ and $R_3$ is H; in Ligand V, $R_1$ is $(CH_2)_{17}CH_3$ and $R_2$ and $R_3$ are H; in Ligand VI, $R_1$ is $CH(CH_3)(CH_2)_{13}CH_3$ and $R_2$ and $R_3$ are H; in Ligand VII, $R_1$ is $(CH_2)_9CH_3$, $R_2$ is H and $R_3$ is $OSi(CH_3)_2C(CH_3)_3$; in Ligand VIII, $R_1$ is $CH_2CH((CH_2)CH_3)((CH_2)_7CH_3)$ and $R_2$ and $R_3$ are H; and in Ligand IX, $R_1$ is $CH_2CH((R_4)(R_5))$, $R_2$ and $R_3$ are H and $R_4$ and $R_5$ are the same or different hydrocarbons having from 6 to 30 carbon atoms.

DETAILED DESCRIPTION OF THE INVENTION

The present invention is an improved process for preparation of a linear aldehyde compound by hydroformylation in the presence of a catalyst system comprising a Group VIII metal and organic ligand containing phosphorous having the structure $P(OR)_2$-OR'O—$P(OR)_2$ or $P(OR)_3$, where R and R' are organic residues which may be the same or different and where the R or R' contain at least one C9 to C40 aliphatic group positioned as a tail extending away from the primary ligand structure rendering the ligand lipophilic.

The preferred ligand of the present invention is a bidentate phosphite ligand having the structure $P(OR)_2$-OR'O—$P(OR)_2$ where R and R' are organic residues and where the R or R' contain at least one C9 to C40 aliphatic group positioned as a tail extending away from the bridging group (R') or the side arms (R) rendering the ligand lipophilic. The term lipophilic when used to modify the term ligand means that the ligand, in a two phase solvent system formed by mixing a polar with a non-polar solvent, will be substantially distributed in the non-polar phase.

The present process combines a ligand structure and a two phase process solvent that allows the easy isolation of reaction products and byproducts from the catalyst system. The term process solvent as used herein means a solvent added initially to the reaction as the reaction solvent or a solvent or a mixture of solvents added following the reaction that is used to extract and separate components of the reaction system. The term extraction means the preferential partitioning or distribution of a compound in one of two immiscible liquid phases.

A suitable starting material for the present process is an ethylenically unsaturated compound having at least one carbon-carbon double bond in the molecule and preferably from 2 to 20 carbon atoms. Examples of such ethylenically unsaturated organic compounds are linear terminal olefinic hydrocarbons, for example, ethylene, propylene, 1-butene, 1-pentene, 1-hexene, 1-octene, 1-nonene, 1-decene, 1-tetradecene, 1-hexadecene, 1-octadecene, 1-eicosene, and 1-dodecene; branched terminal olefinic hydrocarbons, for example, isobutene and 2-methyl-1-butene; linear internal olefinic hydrocarbons, for example, cis- and trans-2-butene, cis- and trans-2-hexene, cis- and trans-2-octene, cis and trans-3-octene; branched internal olefinic hydrocarbons, for example, 2,3-dimethyl-2-butene, 2-methyl-2-butene, and 2-methyl-2-pentene; terminal olefinic hydrocarbon-internal olefinic hydrocarbon-internal olefinic hydrocarbon mixtures, for example, octenes prepared by dimerization of butenes; olefin oligomer isomer mixture from butadiene, dimer to tetramer of lower butadiene olefins including propylene, n-butene, isobutene or the like; and cycloaliphatic olefinic hydrocarbons, for example, cyclopentene, cyclohexene, 1-methylcyclohexene, cyclooctene, and limonene.

The present invention is especially directed to hydroformylation process in which a linear aldehyde compound is prepared starting from internally unsaturated organic compounds with from 6 to 20 carbon atoms such as alkyl pentenoates, pentenoic acids or pentenenitriles.

The ethylenically unsaturated organic compound used in the present process may be substituted with one or more functional groups containing a heteroatom such as oxygen, sulfur, nitrogen, or phosphorous. Examples of these heteroatom-substituted unsaturated organic compounds include vinyl methyl ether, methyl oleate, oleyl alcohol, methyl 2-pentenoate, methyl 3-pentenoate, methyl 4-pentenoate, 3-pentenoic acid, 4-pentenoic acid, 3-pentenenitrile, 4-pentenenitrile, 1,7-octadiene, 7-octen-1-al, acrylonitrile, acrylic acid esters, methyl acrylate, methylacrylic acid esters, methyl methacrylate, acrolein, and other substituted ethylenically unsaturated compounds.

A special class of internally unsaturated organic compounds useful in the present process is 3-pentenenitrile, 3-pentenoic acid, and C1–C6 alkyl 3-pentenoate ester compounds. The linear aldehydes prepared by the present process starting from this class of compounds may advantageously be used in the preparation of e-caprolactam or adipic acid, which are precursors for Nylon-6 and Nylon-6,6 respectively. Examples of C1–C6 alkyl 3-pentenoates are methyl, ethyl, isopropyl, tert-butyl-, pentenyl- and cyclohexyl 3-pentenoate. Methyl and ethyl 3-pentenoate esters are preferred because they are more readily available.

The 3-pentenenitrile, 3-pentenoic acid and C1–C6 alkyl 3-pentenoate ester compounds may be present in mixtures containing respectively: 2- and 4-pentenenitrile; 2- and 4-pentenoic acid; and C1–C6 alkyl 2- and 4-pentenoate ester compounds. Because these compounds react in a similar fashion as their corresponding 3-isomers to the desired linear aldehyde, the mixture of isomers can be directly used in the process according to the present invention.

The reaction conditions of the hydroformylation process according to this invention are in general the same as used in a conventional process, described for example in U.S. Pat. No. 4,769,498, and will be dependent on the particular starting ethylenically unsaturated organic compound. For example, the temperature can be from ambient temperature to 200° C., preferably from about 50° C. to 150° C., and more preferably from 90° to 110° C. The pressure may vary from atmospheric pressure to 20 mPa, preferably from 0.15 to 10 mPa, and more preferably from 0.2 to 5 mPa. The pressure is, as a rule, equal to the combined hydrogen and carbon monoxide partial pressure. However, extra inert gasses may also be present. The molar ratio of hydrogen: carbon monoxide is generally between 10:1 and 1:10 and preferably between 6:1 and 1:2.

The formation of aldehydes by hydroformylation, particularly in a continuous process, often times produces high boiling products that are formed from the condensation of the aldehyde reaction products. These high boiling materials are particularly difficult to remove from the catalyst reaction system (the combination of the phosphorous bidentate ligand and the Group VIII metal ion). In some cases the desired aldehyde product may, itself, be high boiling and difficult to separate from the catalyst system. The present invention provides, through the proper selection of the ligand structure for the catalyst system and the selective use of solvents, a process in which the high boiling reaction products and byproducts may be easily separated from the catalyst system.

In forming the catalyst system of the present invention, the amount of Group VIII metal (compound) is not specially limited, but is optionally selected so that favorable results can be obtained with respect to catalyst activity and process economy. In general, the concentration of Group VIII metal in the reaction medium is between 10 and 10,000 ppm and more preferably between 50 and 500 ppm, calculated as free metal. Although any Group VIII metal may be used in the present process, rhodium is preferred.

Although the molecular structure of the ligand, as described below, is essential to the present invention, the molar ratio of the phosphorous ligand to Group VIII metal is not specially limited, but is optionally selected so that favorable results can be obtained with respect to catalyst activity and desired aldehyde selectivity. This ratio generally is from about 0.5 to 100 and preferably from 1 to 10 (moles ligand/mole metal).

Although the ligand of the present invention may be monodentate or bidentate, the preferred ligands of the present invention are bidentate organic phosphite ligands having two trivalent phosphorous atoms wherein the ligand contains at least one C9 to C40 aliphatic group positioned on the backbone or side arm ring structures of the ligand. Bidentate ligands having two trivalent phosphorous may be of the class of phosphine, phosphite, phosphinite, or phosphonite.

The structure of any ligand used in a hydroformylation catalyst system is generally selected such that backbone and side arms of the ligand structure provide the desired selectivity and activity. The term backbone refers to the bridging group between the two phosphorus atoms, and the term side arms refer the non-bridging groups attached to the phosphorus atoms.

Many backbone and side arm structures of bidentate ligands known for the production of aldehydes by hydroformylation may be modified for use in the present invention by adding to the ligand at least one C9 to C40 aliphatic group substituted for a hydrogen or for some R group of the aromatic ring backbone or side arm structure. Also ligands known for hydroformylation that already have at least one C9 to C40 aliphatic group on the backbone or side arm structures of the ligand may be used in the present invention. By the term modifying is meant the substitution of the aliphatic group of the invention on a ligand already synthesized or the changing the synthesis of the ligand so that the final structure contains at least one C9 to C40 aliphatic group.

The ligand structures of the present invention provide long chain aliphatic group or tails that extend from the ligand structure causing the ligand to become preferentially soluble in a non-polar solvent. The substitution of the aliphatic group on a backbone or side arm position will contribute little if any to a change in the activity or selectivity of the ligand as used in the catalyst system for hydroformylation. Thus by adapting the ligand to be preferentially soluble in a non-polar solvent, the present invention provides a ligand property that can work together with the two phase process solvent to make the separation of ligand and product simple and easy, while maintaining the activity and selectivity of the basic ligand structure (that is the activity and selectivity of the ligand not having the substitution of a smaller group by a C9 to C40 aliphatic group). Ligands of the following structures are preferred in the present invention because of their activity and selectivity towards linear aldehydes. As noted below the basic structure for Ligands I, II and III is structure A on the left; the basic structure for Ligands IV to IX is structure B on the right:

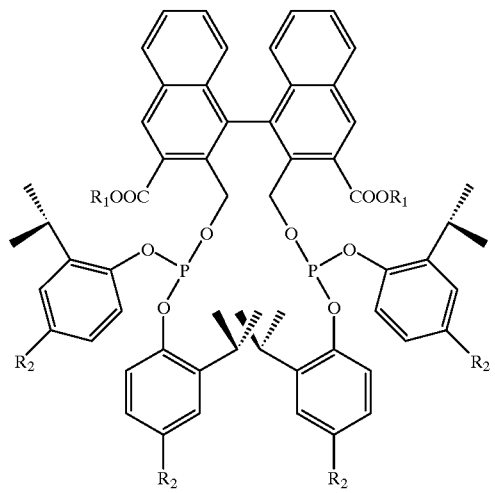

Structure A for Ligands
I to III

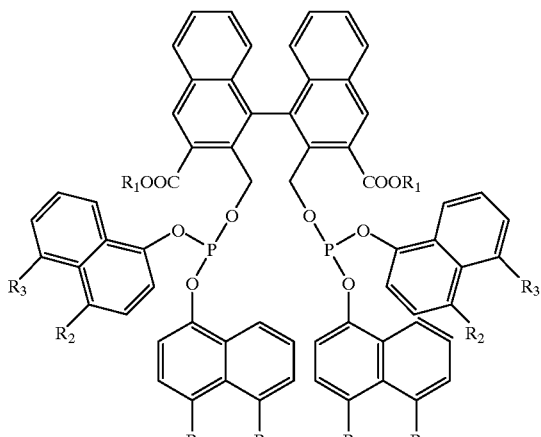

Structure B for Ligands
IV to IX where in Ligand I, $R_1$ is $(CH_2)_9CH_3$ and $R_2$ is H; in Ligand II, $R_1$ is $(CH_2)_9CH_3$ and $R_2$ is $CO(CH_2)_8CH_3$; in Ligand III, $R_1$ and $R_2$ are $(CH_2)_9CH_3$; in Ligand IV, $R_1$ is $(CH_2)_9CH_3$, $R_2$ is $O(CH_2)_9CH_3$ and $R_3$ is H; in Ligand V, $R_1$ is $(CH_2)_{17}CH_3$ and $R_2$ and $R_3$ are H; in Ligand VI, $R_1$ is $CH(CH_3)(CH_2)_{13}CH_3$ and $R_2$ and $R_3$ are H; in Ligand VII, $R_1$ is $(CH_2)_9CH_3$, $R_2$ is H and $R_3$ is $OSi(CH_3)_2C(CH_3)_3$; in Ligand VIII, $R_1$ is $CH_2CH((CH_2)_5CH_3)((CH_2)_7CH_3)$ and $R_2$ and $R_3$ are H; and in Ligand IX, $R_1$ is $CH_2CH((R_4)(R_5))$, $R_2$ and $R_3$ are H and $R_4$ and $R_5$ are the same or different hydrocarbons having from 6 to 30 carbon atoms.

The second aspect of the present invention is the use of a two phase process solvent. As described below, the two phase solvent mixture or process solvent may be used in three ways in the practice of the present invention. It may be used as the reaction solvent; or one of the components of the two phase solvent mixture may be used as the reaction solvent and the other component added following the hydroformylation to serve to extract and separate reaction products from the catalyst system; or the hydroformylation reaction may be carried out with the ethylenically unsaturated compound also functioning as the reaction solvent; then following the hydroformylation, the two phase process solvent or mixture is added to the reaction mixture to extract and separate products from the catalyst system.

Generally when one solvent does not dissolve in another solvent, or when a first solvent has a low or limited solubility in a second solvent, the two solvents are said to be immiscible. When immiscible solvents are mixed together, they separate into two phases—the less dense phase floating on top of the more dense phase. Also generally when a mixture of two or more solvents form separate phases, one phase is said to polar relative to the other. Polar and non-polar are relative terms, but polar solvents are generally those that contain electronegative atoms such as oxygen or nitrogen, are of lower molecular weights and mix with water. Non-polar solvents are those that contain primarily hydrogen and carbon, that do not mix with water and that mix readily with oil. As used herein, the term polar means to hydrophilic or lipophobic; while the term non-polar means hydrophobic or lipophilic. Thus, a lipophilic ligand is one that is preferentially soluble in a non-polar solvent or in the more non-polar of a two solvent mixture.

To form the two phase process solvent of the present invention, one mixes a polar and a non-polar solvent or mixtures of polar and non-polar solvents to form two phases. One solvent or solvent mixture must be more lipophilic than the other. As described above, this two phase solvent mixture may be present as the initial reaction solvent for the hydroformylation. It may be added as a two phase mixed solvent following the hydroforymlation to function as an extraction medium.

Or in another way to practice the present invention, a single solvent may be added to the reaction mixture causing the formation of a two phase mixture from which the desired component of the hydroformylation reaction system may be isolated.

In selecting solvent components for the two phase solvent mixture, it is only essential that the two components form two separate phases when mixed together. The ligand structures of the present invention, having extended aliphatic tails that may be as long as C40, cause the ligand to be preferentially soluble in the non-polar component of the two phase solvent mixture. The present invention also allows for the adjustment of the polarity of the ligand by the choice of longer tails and a greater number of tails being used to provide a more non-polar ligand.

Examples of polar compounds suitable for forming the two phase solvent mixture include water, dimethylacetamide (DMAc), dimethyl sulfoxide (DMSO), methanol, ethanol, dimethylforamide (DMF), adiponitrile (AND), acetonitrile and N-methyl pyrrolidone(NMP).

Compounds such as C5 to C20 hydrocarbons including linear, branched, cyclic or aromatic compounds are examples of compounds that may be used as the non-polar component of the two phase solvent mixture. Higher molecular weight alcohols, aldehydes, esters or ketones may also be used as the non-polar component. Examples of non-polar compounds suitable in the process of the present invention include hexane, cyclohexane, hexene, petroleum ethers and naphta. For an aromatic solvent used in the practice of the present invention, it is preferred that the aromatic solvent molecule have aliphatic side chains to ensure that it is non-polar enough to form a second phase when mixed with the reaction products of the hydroformylation.

If the reaction conditions are at sufficient pressure, even C4 hydrocarbons could be used as the non-polar component of the solvent mixture.

In the practice of the present invention, a non-polar solvent may be added to the reaction mixture after the hydroformylation reaction is completed, but before any products are isolated from the mixture. Such a process would occur as follows: (a) reacting an ethylenically unsaturated compound by hydroformylation in the presence a solvent and the catalyst system of the present invention, (b) adding a non-polar solvent to the reaction product of step (a) so that two phases are formed and allowing the catalyst system to be extracted into the non-polar solvent, (c) isolation of the non-polar solvent layer, (d) evaporation of the non-polar solvent to isolate the catalyst system, (e) returning the isolated catalyst system to step (a).

Another way to practice the present invention is by removing any volatiles, including reaction products prior to addition of a non-polar solvent. Such a process would occurs as follows: (a) reacting an ethylenically unsaturated compound by hydroformylation in the present of a polar solvent or an excess of the ethylenically unsaturated compound and the catalyst system of the present invention, (b) removal of volatiles from the reaction media of step (a), (c) dissolving the catalyst system in a non-polar solvent such as a C5 to C20 hydrocarbon solvent so that two layers are formed or adding a two phases solvent mixture to the reaction mixture dissolving the catalyst system in the non-polar phase, (d) isolation of the non-polar solvent containing the catalyst system, (e) evaporation of the hydrocarbon solvent to isolate the catalyst system, (f) returning the isolated catalyst system to step (a) and recovery of either solvent or products distributed in the polar phase. In the case of this method of practicing the present invention, the reaction solvent may be an the olefinic reactant.

In another way of practicing the present invention, the reaction would be run in a two phase reaction solvent. Following reaction, the phase can be separated by conventional means and the product recovered and the catalyst may be recycled for further reaction.

The extraction step in the present invention may be carried out at room temperature and atmospheric pressure or at other conditions that are suitable in the overall processing of batch or continuous hydroformylation operations. For example, pressures for extraction may be from 0.1 to 1 Pa, with a range of 0.1 to 0.2 Pa being preferred, and temperatures for the extraction may be from 0 to 120° C., with a preferred range from 15 to 50° C.

The preferred way to practice the present invention is to allow the hydroformylation reaction to take place in an excess of the ethylenically unsaturated compound. Then following the hydroformylation reaction to add a two phase solvent mixture to partition and extract the reaction products in the polar phase of the solvent mixture and the catalyst system in the non-polar phase.

The process of this invention may be run in either a continuous or batch mode. In general for large scale industrial processes, a continuous mode is preferred, while batch mode is more practical for smaller scale reactions.

The invention is illustrated by but not intended to be limited to the following examples.

EXAMPLES

Synthesis of a lipophilic ligand:

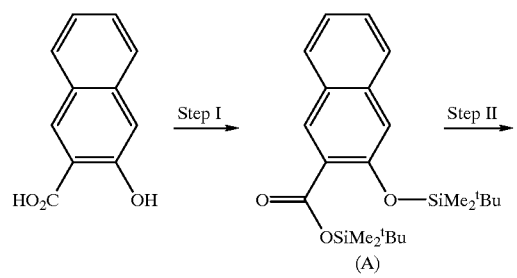
(A)

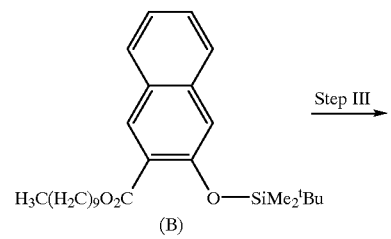
(B)

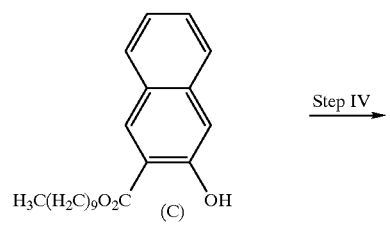
(C)

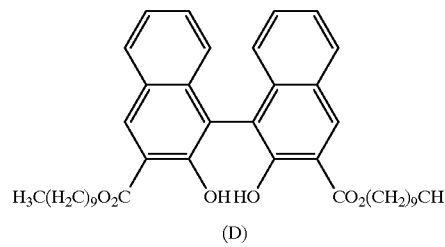
(D)

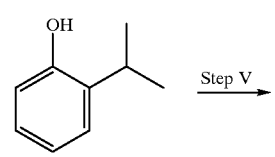

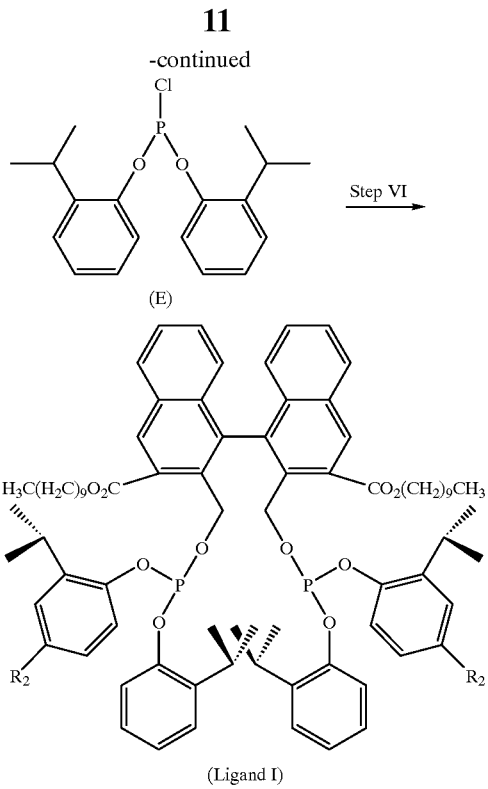

The synthesis of ligand-I was carried out in the following series of steps forming compounds A to E.

I. Synthesis of tert-Butyldimethylsilyl 3-(tert-butyldimethylsilyloxy)-2-naphthoate, Compound A: To a solution of 30 g (0.16 mol) of 3-hydroxy-2-naphthoic acid and 51 g (0.34 mol) of tert-butyldimethylsilyl chloride in 600 mL of tetrahydrofuran was added dropwise 64 g (0.64 mol) of triethylamine under nitrogen. The mixture was stirred for four hours at room temperature, triethylamine hydrochloride was filtered, and the solvent was evaporated. The residue was poured into water (500 mL) and extracted with petroleum ether (500 mL). The organic layer was washed with saturated aqueous sodium bicarbonate, dried over magnesium sulfate and filtered.

The solvent was evaporated under vacuum to yield 58 g (87%) of (A) as a yellow liquid.

II. Synthesis of decyl 3-(tert-Butyldimethylsilyloxy)-2-naphthoate (Compound B): Under nitrogen, 17.5 mL (0.20 mol) of oxalyl chloride were added dropwise to a solution of 58 g (0.14 mol) of Compound A in 300 mL of dichloromethane containing 60 drops of dimethylformamide. The mixture was stirred overnight at room temperature, and then the solvent was evaporated under vacuum. To the residue was slowly added a solution of 24 g (0.15 mole) of 1-decanol and 33 g (0.42 mol) of pyridine in 200 ml of diethyl ether under nitrogen. The mixture was stirred overnight at room temperature. Then the pyridinium hydrochloride was filtered and the solvent was evaporated under vacuum. Hexane was added, the mixture was stirred for 5 minutes and then filtered through silica gel. Hexane was evaporated under vacuum to yield 62 g of Compound B as a yellow liquid.

III. Synthesis of decyl-3-hydroxy-2-naphtoate (Compound C): To a solution of 49 g (0.11 mol) of Compound B in 300 mL of tetrahydrofuran was added a solution of 80 g (0.25 mol) of tetrabutylammonium fluoride in 200 mL of tetrahydrofuran. The mixture was stirred for one hour at room temperature, and then the solvent was evaporated under vacuum. The residue was dissolved in dichloromethane and washed with aqueous ammonium chloride and saturated aqueous sodium bicarbonate. The organic layer was dried over magnesium sulfate and filtered before the solvent was evaporated. The product, Compound C, was purified by filtration over silica gel using 3% ether/hexane as the eluent. Yield 92%.

IV. Synthesis of 4,4'-Bi-decyl 3-hydroxy-2-naphthoate (Compound D): To a solution of 23 g (0.071 mol) of Compound C in 400 mL toluene was added 1.6 g (7.1 mmol) of Cu(OH)Cl-TMEDA where TMEDA stands for N,N,N',N'-tetramethylethylenediamine. The reaction mixture was heated at 100° C. under an atmosphere of oxygen overnight, and the progress of the reaction was monitored by thin layer chromatography. Once Compound C was totally converted, the reaction mixture was filtered through silica gel, rinsed with dichloromethane before removing the solvent under vacuum. Recrystallization from methanol gave 21 g (91%) of Compound D as yellow crystals.

V. Synthesis of Bis (2-isopropylphenyl)-phosphorochloridite (Compound E): To a solution of 20 g (0.15 mol) of 2-isopropylphenol and 16 g (0.16 mol) of triethylamine in 200 ml of hexane was slowly added a solution of 14.8 g (0.07 mol) of diisopropylphosphoramidous dichloride in 200 mL of hexane. The mixture was stirred overnight at room temperature, then filtered through alumina and washed with dichloromethane. The solvent was removed under vacuum, and the residue (9 g, 0.027 mol) was dissolved in 200 mL of cyclohexane. Dry HCl was bubbled through the solution for one hour. The excess HCl was purged by bubbling nitrogen through the reaction mixture. The reaction mixture was then transferred into a dry box. The diethylamine hydrochloride filtered, and the solution evaporated under vacuum to give 6.2 g of Compound E as a yellow oil.

Ligand-I: 5 ml of tetrahydrofuran was added dropwise along with a solution of 4 g (0.006 mole) of Compound D and 2.3 g (0.02 mol) of triethylamine in 50 mL of tetrahydrofuran under nitrogen to a solution of 6.2 g (0.018 mol) of Compound E. The reaction mixture was stirred overnight at room temperature, filtered and evaporated. The reside was treated with 10 mL isopropyl alcohol and 2 g of triethylamine. After stirring for one hour, the solvent was evaporated, pentane was added and the mixture filtered through alumina. Recrystallization from pentane gave 5 g of Ligand-I as white crystals.

EXAMPLE 1: Hydroformylation in a Two phase Solvent

A solution containing 0.28 g of Ligand-I, 0.032 g of rhodiumdicarbonylacetylacetonate, 1.44 g of O-dichlorobenzene (internal standard) and 30.31 g of methyl 3-pentenoate were mixed with 29.92 g of octane (non-polar component) and 30.87 g of adiponitrile (polar component). This two phase system was loaded into a 100 mL autoclave and heated with vigorous stirring under 150 psi CO/H2(1:1) at 105° C. for 8 hours. A GC sample was taken after 8 hours and homogenized by adding acetone. The analysis shows (mole%):methyl 4-pentenoate (M4P) 0.63%, methyl 2-pentenoate (M2P) 4.91%, methyl valerate (MV) 4.96%, methyl 3-pentenoate (M3P) 13.92%, methyl 3-formylvalerate (3FMVA) 2.89%, methyl 4-formylvalerate (4FMVA) 3.25%, methyl 5-formyl-valerate (5FMVA) 68.87%. Once the autoclave reached 30° C., the content was transferred into a nitrogen purged dry box. The phases were separated and analyzed by X-ray Florescence (XFR) for Rh and P. Top phase 590 ppm P, 433 ppm Rh; bottom phase 20 ppm P, 10 ppm Rh. GC analysis: Top phase (octane) M4P 0.0%, M2P 13.49%, MV 19.08%, M3P 35.29%, 3FMVA 1.95%, 4FMVA 1.85%, 5FMVA 28.34%; Bottom phase (adiponitrile) M4P 0.5%, M2P 3.93%, MV 3.58%, M3P 12.1%, 3FMVA 2.99%, 4FMVA 3.42%, 5FMVA 73.48%; moles top phase/moles bottom phase=7.7/92.3.

EXAMPLE 2: Catalyst Extraction and Recycle

A solution containing 0.448 g of Ligand-I, 0.044 g of rhodiumdicarbonylditertbutylacetylacetonate and 65.054 g of methyl-3-pentenoate was loaded into a 100 mL autoclave and heated with vigorous stirring under 150 psi CO/H2(1:1) at 105° C. for 8 hours. Once the autoclave reached 30° C. the content was transferred into a nitrogen purged dry box. The effluent (reaction mixture) from the autoclave was weighed and combined with equal weights of hexane and acetonitrile (two phase process solvent). The top layer was saved and the bottom layer extracted twice with the same amount of hexane. All the hexane layers were combined and under high vacuum hexane was removed. Methyl 3-pentenoate was added to the residue as shown in Table 1 and the hydroformylation reaction was run again. A 100 uL sample was taken each cycle to monitor the performance of the catalyst upon recycle. Table 2 indicates the composition (mmol/g) as a function of cycle number.

TABLE 1

|  | $W_{residue}$ (g) | M3P (g) | $W_{out} - W_{in}$ (g) | Time (h) |
| --- | --- | --- | --- | --- |
| Cycle #1 |  | 65.06 | 8.27 | 6.00 |
| Cycle #2 | 9.86 | 64.70 | 9.13 | 6.00 |
| Cycle #3 | 16.05 | 66.53 | 11.60 | 8.00 |
| Cycle #4 | 18.09 | 54.67 | 13.16 | 8.00 |
| Cycle #5 | 8.79 | 61.58 | 8.88 | 6.00 |
| Cycle #6 | 8.85 | 61.72 | 8.11 | 6.00 |
| Cycle #7 | 7.00 | 67.28 | 7.95 | 6.00 |

TABLE 2

|  | M4P | M2P | MV | M3P | 3FMVA | 4FMVA | 5FMVA |
| --- | --- | --- | --- | --- | --- | --- | --- |
| Cycle #1 | 0.11 | 0.40 | 0.15 | 1.92 | 0.22 | 0.26 | 4.25 |
| Cycle #2 | 0.10 | 0.41 | 0.14 | 2.50 | 0.20 | 0.24 | 3.65 |
| Cycle #3 | 0.12 | 0.41 | 0.13 | 3.17 | 0.19 | 0.23 | 3.22 |
| Cycle #4 | 0.11 | 0.46 | 0.16 | 2.13 | 0.23 | 0.28 | 4.01 |
| Cycle #5 | 0.08 | 0.39 | 0.13 | 2.49 | 0.21 | 0.25 | 3.08 |
| Cycle #6 | 0.12 | 0.38 | 0.12 | 2.69 | 0.20 | 0.24 | 3.90 |
| Cycle #7 | 0.14 | 0.37 | 0.12 | 3.29 | 0.23 | 0.26 | 3.99 |

EXAMPLE 3:

The following example illustrates a high boiler purge in the process of the present invention. A 100 mL autoclave was charged with 80 g of a solution prepared dissolving 1.31 g of Ligand-V, described above, 0.054 of rhodiumdicarbonylacetyl-acetonate and 100 g of methyl 3-pentenoate (excess ethylenically unsaturated compound). The autoclave heated with vigorous stirring under 150 psi CO/H2(1:1) at 105° C. for 5 hours. Once the autoclave reached 30° C. the content was transferred into a nitrogen purged dry box and the product distilled under high vacuum. The residue (including high boiling byproducts and the catalyst system) was dissolved in methyl 3-pentenonate and the hydroformylation experiment repeated 10 times. The analysis for the 10 experiments is shown in Table 3. The residue (polar solvent) (17.2 g) from cycle 10 was combined with 75 ml of hexane (addition of a non-polar phase to form the process solvent). The phases were separated and the bottom layer was extracted twice with 75 mL of hexane. The hexane extracts were combined, hexane was removed under vacuum and the residue (1.1 g) was dissolved in methyl 3-pentenoate. The bottom layer weighed 15.6 g indicating 90% efficiency for the removal of high boilers. The hydroformylation experiment was repeated again. The analysis for this experiment, Cycle 11, is also shown in Table 3. Table 3 indicates the composition (mmol/g) as a function of cycle number.

TABLE 3

|  | M4P | Mc2P | MV | M3P | Mt2P | M2FV | M3FV | M4FV | M5FV |
| --- | --- | --- | --- | --- | --- | --- | --- | --- | --- |
| Cycle #1 | 0.00 | 0.01 | 0.25 | 0.32 | 0.35 | 0.06 | 0.18 | 0.24 | 5.03 |
| Cycle #2 | 0.01 | 0.02 | 0.29 | 0.42 | 0.57 | 0.05 | 0.15 | 0.26 | 4.68 |
| Cycle #3 | 0.00 | 0.02 | 0.26 | 0.36 | 0.45 | 0.09 | 0.20 | 0.29 | 4.78 |
| Cycle #4 | 0.00 | 0.01 | 0.24 | 0.31 | 0.45 | 0.05 | 0.20 | 0.30 | 4.23 |
| Cycle #5 | 0.01 | 0.01 | 0.24 | 0.38 | 0.39 | 0.04 | 0.20 | 0.28 | 4.61 |
| Cycle #6 | 0.01 | 0.01 | 0.24 | 0.36 | 0.30 | 0.07 | 0.21 | 0.26 | 4.31 |
| Cycle #7 | 0.01 | 0.02 | 0.26 | 0.33 | 0.61 | 0.04 | 0.13 | 0.27 | 3.55 |
| Cycle #8 | 0.01 | 0.02 | 0.29 | 0.33 | 0.64 | 0.06 | 0.12 | 0.28 | 4.02 |
| Cycle #9 | 0.01 | 0.01 | 0.23 | 0.32 | 0.31 | 0.14 | 0.16 | 0.22 | 4.18 |
| Cycle #10 | 0.01 | 0.02 | 0.27 | 0.39 | 0.51 | 0.02 | 0.11 | 0.20 | 3.96 |
| Cycle #11 | 0.01 | 0.02 | 0.31 | 0.57 | 0.40 | 0.05 | 0.17 | 0.22 | 4.73 |

EXAMPLE 4: Catalyst Extraction from 3-Pentenenitrile Hydroformylation Mixture.

The following example illustrates catalyst separation from product according to the present invention when a non polar solvent is added to the reaction mixture in the 3-pentenitrile hydroformylation to 5-formylvaleronitrile.

A solution containing 1.75 g of Ligand-IX ($R_4$=$(CH_2)_{11}CH_3$, $R_5$=$(CH_2)$ $CH_3$), 0.058 g of rhodiumdicarbonylacetylacetonate and 70 g of 3-pentenenitrile were loaded into a 100 mL autoclave and heated with vigorous stirring under 50 psi $CO/H2(1:1)$ at 95° C. for 3 hours. Once the autoclave reached 30° C. the contents were transferred into a nitrogen purged dry box. A sample from the reactor was analyzed by GC. The results showed: 3-pentenenitrile conversion 97%, 5-formylvaleronitrile selectivity 65%, and aldehyde linearity 79%. The effluent (reaction mixture) from the autoclave was weighed and combined with equal weights of hexane. The top layer (hexane) and bottom layer (product) were analyzed. The results showed:

Top layer: 59 ppm Rh, 285 ppm P 3-pentenenitrile: 5.28%

5-formylvaleronitrile: 17.5% valeronitrile: 61.5%

Bottom layer: 19 ppm Rh, 181 ppm P 3-pentenenitrile: 1.98%

5-formylvaleronitrile: 63.4% valeronitrile: 15.4%

What is claimed:

1. A process for preparation of a linear aldehyde comprising reacting an ethylenically unsaturated compound by hydroformylation in the presence of a catalyst system composed of a Group VIII metal, an organic phosphite ligand and a reaction solvent wherein the organic phosphite ligand is a ligand containing phosphorous having the structure $P(OR)_2$-OR'O-$P(OR)_2$ or $P(OR)_3$, where R and R' are organic residues which may be the same or different and where the R or R' contain at least one C9 to C40 aliphatic group positioned as a tail extending away from the primary ligand structure rendering the ligand lipophilic and wherein the reaction solvent is a two phase mixture of an organic compound having from 5 to 20 carbon atoms and polar solvent.

2. A process for hydroformylation of an ethylenically unsaturated compound wherein reaction products including high boiling reaction products are separated from the catalyst system comprising the steps of:

(a) reacting in a reaction solvent to form a reaction mixture the ethylenically unsaturated compound in the presence of a catalyst system composed of a Group VIII metal and organic phosphite ligand having the structure $P(OR)_2$-OR'O—$P(OR)_2$ or $P(OR)_3$, where R and R' are organic residues which may be the same or different and where the R or R' contain at least one C9 to C40 aliphatic group positioned as a tail extending away from the primary ligand structure rendering the ligand lipophilic;

(b) adding a non-polar solvent to the reaction mixture to form two phases, one a polar phase predominately formed from the reaction products and one formed predominately from the non-polar solvent and the catalyst system such that the reaction products including the high boiling reaction products of the hydroformylation remain in the polar phase and the catalyst system is partitioned substantially into the non-polar phase; and (c) separating the two phases and isolating the reaction products from the polar phase and the catalyst from the non-polar phase.

3. The process of claim 1 or 2 wherein ligand is a bidentate phosphite ligand, $P(OR)_2$-OR'O—$P(OR)_2$, containing at least one C9 to C40 aliphatic group positioned on R or R'.

4. The process of claim 1 or 2 wherein the reaction solvent is the ethylenically unsaturated compound.

5. The process of claim 2 wherein volatile are removed from the reaction mixture of step (a) before the addition of the non-polar solvent of step (b).

6. The process of claim 2 wherein steps (a) and (b) are combined and the hydroformylation is carried out in a two phase reaction solvent.

7. The process of claim 2 wherein the recovered catalyst is returned to step (a) and the steps are repeated.

8. The process of claim 1 or 2 wherein the non-polar solvent is chosen from the group of C5 to C20 hydrocarbon solvents.

9. The process of any one of claims 1 or 2, wherein the ethylenically unsaturated compound is chosen from the group consisting of 3-pentenoic acid, C1 to C6 alkyl esters of 3-pentenoic acid, 3-pentenenitrile, and 4-pentenenitrile.

10. The process of claim 1 or 2 wherein the organic ligand is chosen from the structures A and B

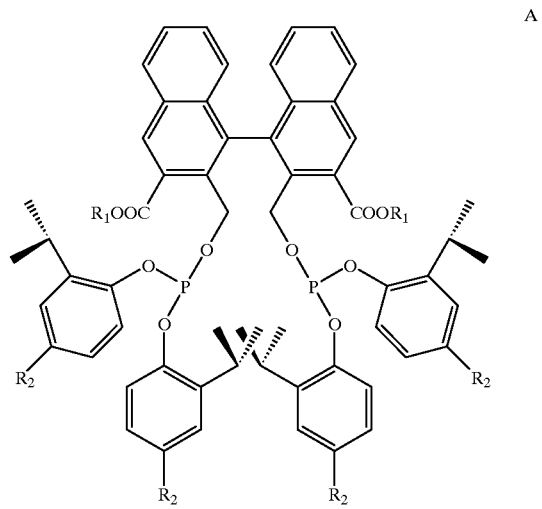

-continued

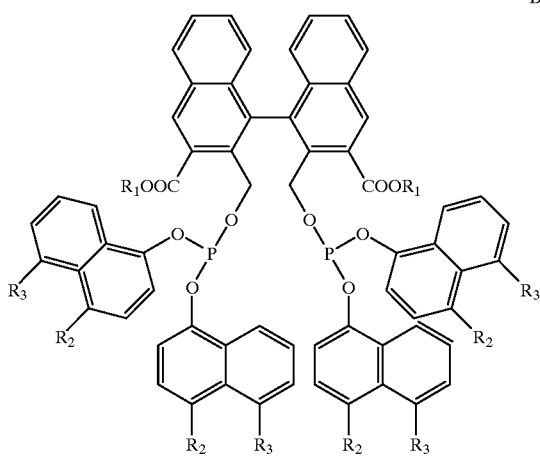

B wherein structures A for Ligands I to III and structures B for Ligands IV to IX; Ligand I, $R_1$ is $(CH_2)_9CH_3$ and $R_2$ is H; Ligand II, $R_1$ is $(CH_2)_9CH_3$ and $R_2$ is $CO(CH_2)_8 CH_3$ ; Ligand III is $R_1$ and $R_2$ are $(CH_2)_9CH_3$; Ligand IV, $R_1$ is $(CH_2)_9CH_3$, $R_2$ is $O(CH_2)_9CH_3$ and $R_3$ is H; in Ligand V, $R_1$ is $(CH_2)_{17}CH_3$ and $R_2$ and $R_3$ are H; in Ligand VI, $R_1$ is $CH(CH_3)$ $(CH_2)$ $1CH_3$ and $R_2$ and $R_3$ are H; in Ligand VII, R1 is $(CH_2)_9CH_3$, $R_2$ is H and $R_3$ is $OSi(CH_3)_2C(CH_3)_3$; in Ligand VIII, $R_1$ is $CH_2CH((CH_2) CH_3) ((CH_2)_7CH_3)$ and $R_2$ and $R_3$ are H; and in Ligand IX, $R_1$ is $CH_2CH((R_4) (R_5))$, $R_2$ and $R_3$ are H and $R_4$ and R5 are the same or different hydrocarbons having from 6 to 30 carbon atoms.

11. An improved hydroformylation process for preparation of a linear aldehyde from a reaction mixture containing an ethylenically unsaturated compound and a catalyst system composed of a Group VIII metal and a bidentate organic phosphite ligand, $P(OR)_2$-OR'O—$P(OR)_2$, having two trivalent phosphorous atoms, P, bridged by a backbone aromatic ring structure, R', and bonded to two sidearm aromatic ring structures, R, wherein the ethylenically unsaturated compound also functions as reaction solvent, the improvement comprising:

forming the catalyst system from a ligand containing at least one C9 to C40 aliphatic group positioned on the backbone or side arm ring structures of the ligand and following hydroformylation of the ethylenically unsaturated compound adding to the reaction mixture a two phase solvent mixture consisting of a polar and a non-polar component so that the reaction products of the hydroformylation are extracted into the polar phase of the solvent mixture and the catalyst system remains substantially in the non-polar phase of the solvent mixture.

12. The process of claim 11 wherein the non-polar solvent is chosen from the group of C5 to 20 hydrocarbon solvents.

13. The process of claim 11 wherein the ethylenically unsaturated compound is chosen from the group consisting of 3-pentenoic acid, C1 to C6 alkyl esters of 3-pentenoic acid, 3-pentenenitrile, and 4-penetenenitrile.

14. The process of claim 11 wherein the organic ligand is chosen from the structures A and B

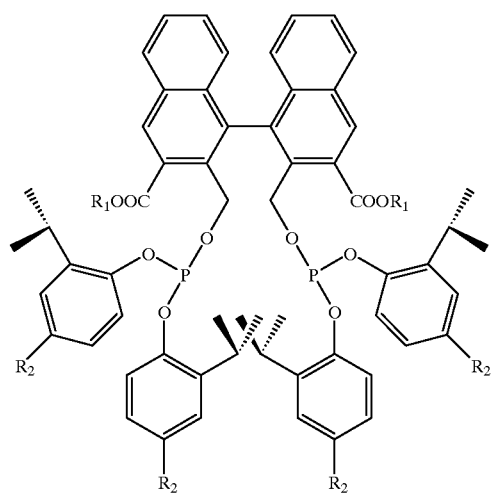

A

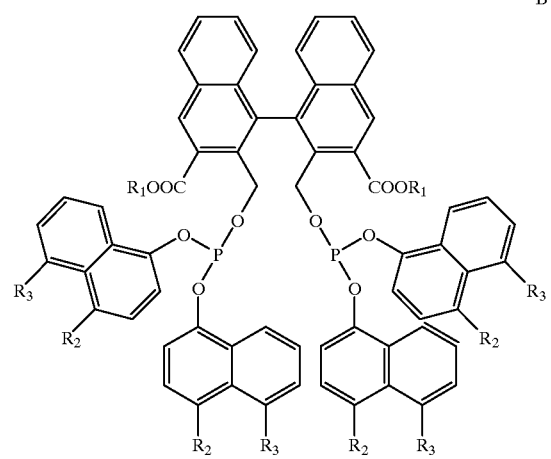

B wherein structures A for Ligands I to III and structures B for Ligands IV to IX; Ligand I, $R_1$ is $(CH_2) CH_3$ and $R_2$ is H; Ligand II, $R_1$ is $(CH_2) CH_3$ and $R_2$ is $CO(CH_2)_8 CH_3$ ; Ligand III is $R_1$ and $R_2$ are $(CH_2)_9CH_3$; Ligand IV, $R_1$ is $(CH_2)_9CH_3$ , $R_2$ is O $(CH_2)_9CH_3$ and $R_3$ is H; in Ligand V, $R_1$ is $(CH_2)_{17}CH_3$ and $R_2$ and $R_3$ are H; in Ligand VI, $R_1$ is CH $(CH_3)$ $(CH_2)_{13}CH_3$ and $R_2$ and $R_3$ are H; in Ligand VII, $R_1$ is $(CH_2)_9CH_3$, $R_2$ is H and $R_3$ is $OSi(CH_3)_2C(CH_3)_3$; in Ligand VIII, $R_1$ is $CH_2CH ((CH_2)_5CH_3) ((CH_2)_7CH_3)$ and $R_2$ and $R_3$ are H; and in Ligand IX, $R_1$ is $CH_2CH( (R_4) (R_5) )$, $R_2$ and $R_3$ are H and $R_4$ and $R_5$ are the same or different hydrocarbons having from 6 to 30 carbon atoms.

15. The process as in claim 1, 2 or 11 wherein the Group VIII metal rhodium.

* * * * *